US008822934B2

(12) United States Patent
Sayeh et al.

(10) Patent No.: US 8,822,934 B2
(45) Date of Patent: Sep. 2, 2014

(54) COLLIMATOR CHANGER

(75) Inventors: Sohail Sayeh, San Ramon, CA (US);
Gopinath R. Kuduvalli, San Jose, CA (US); Hendricus J. Wolters, Menlo Park, CA (US); Kenneth W. Schulze, Scotts Valley, CA (US); Michael J. Stratford-Collins, San Mateo, CA (US); Monica A. Condit, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1982 days.

(21) Appl. No.: 11/592,803

(22) Filed: Nov. 3, 2006

(65) Prior Publication Data
US 2008/0107239 A1 May 8, 2008

(51) Int. Cl.
G21K 1/02 (2006.01)
B23Q 3/155 (2006.01)
B25J 15/04 (2006.01)
A61N 5/10 (2006.01)

(52) U.S. Cl.
CPC .. B25J 15/04 (2013.01); A61N 5/10 (2013.01)
USPC ............................ 250/363.1; 378/148; 483/58

(58) Field of Classification Search
USPC .......... 250/363.1, 492.1, 492.3, 505.1, 506.1; 378/65, 145, 147, 148, 151–153, 160, 378/161; 483/1, 16, 20, 25, 26, 58, 901, 483/902
See application file for complete search history.

(56) References Cited

U.S. PATENT DOCUMENTS

| | | | |
|---|---|---|---|
| 3,982,133 A * | 9/1976 | Jupa et al. ...................... 378/148 |
| 4,583,892 A | 4/1986 | Armbruckner | |
| 4,604,787 A * | 8/1986 | Silvers, Jr. ...................... 483/55 |
| 4,758,726 A * | 7/1988 | Douma et al. ............. 250/363.1 |
| 4,794,629 A * | 12/1988 | Pastyr et al. .................. 378/152 |
| 4,883,939 A | 11/1989 | Sagi | |
| 5,018,266 A | 5/1991 | Hutchinson et al. | |
| 5,131,706 A | 7/1992 | Appleberry | |
| 5,189,687 A * | 2/1993 | Bova et al. ....................... 378/65 |
| 5,210,422 A * | 5/1993 | Kurakake et al. .......... 250/363.1 |
| 5,496,249 A | 3/1996 | Buggle et al. | |
| 5,519,223 A * | 5/1996 | Hug et al. .................. 250/363.1 |
| 5,608,224 A | 3/1997 | Alvord | |
| 5,945,684 A * | 8/1999 | Lam et al. .................. 250/492.3 |
| 5,961,926 A | 10/1999 | Kolb et al. | |
| 6,052,436 A | 4/2000 | Huttner et al. | |
| 6,366,641 B1 * | 4/2002 | Whitham ........................ 378/65 |
| 6,441,377 B1 | 8/2002 | Hug et al. | |
| 6,614,036 B1 * | 9/2003 | Reinstein ................... 250/492.3 |
| 6,703,512 B1 | 3/2004 | Grinter et al. | |
| 6,857,995 B2 | 2/2005 | Maeda | |
| 6,949,055 B2 | 9/2005 | Ferrari et al. | |
| 7,142,634 B2 * | 11/2006 | Engler et al. ..................... 378/65 |
| 7,295,648 B2 * | 11/2007 | Brown .............................. 378/65 |
| 7,693,260 B2 * | 4/2010 | Gertner et al. .................. 378/65 |
| 7,792,249 B2 * | 9/2010 | Gertner et al. .................. 378/65 |

(Continued)

OTHER PUBLICATIONS

PCT International Search Report and Written Opinion of the International Searching Authority, PCT/US2007/021653 filed Oct. 9, 2007, mailed May 21, 2008.

(Continued)

Primary Examiner — Bernard E Souw
(74) Attorney, Agent, or Firm — Lowenstein Sandler LLP

(57) ABSTRACT

An automatic collimator changer of a radiation treatment system.

18 Claims, 16 Drawing Sheets

(56) References Cited

U.S. PATENT DOCUMENTS

| | | | |
|---|---|---|---|
| 8,093,572 B2* | 1/2012 | Kuduvalli | 250/505.1 |
| 2002/0122531 A1* | 9/2002 | Whitham | 378/137 |
| 2005/0089141 A1* | 4/2005 | Brown | 378/65 |
| 2005/0234327 A1* | 10/2005 | Saracen et al. | 600/407 |
| 2006/0020201 A1 | 1/2006 | Caruba | |
| 2006/0193441 A1 | 8/2006 | Cadman | |
| 2008/0107239 A1* | 5/2008 | Sayeh et al. | 378/148 |
| 2009/0001296 A1* | 1/2009 | Kuduvalli | 250/505.1 |
| 2009/0003528 A1* | 1/2009 | Ramraj et al. | 378/119 |
| 2009/0003975 A1* | 1/2009 | Kuduvalli et al. | 414/146 |
| 2009/0116616 A1* | 5/2009 | Lu et al. | 378/65 |
| 2009/0175406 A1* | 7/2009 | Zhang et al. | 378/8 |
| 2010/0069920 A1* | 3/2010 | Naylor et al. | 606/130 |
| 2011/0004094 A1* | 1/2011 | Stubbs et al. | 600/424 |
| 2012/0158017 A1* | 6/2012 | Naylor et al. | 606/130 |
| 2012/0174317 A1* | 7/2012 | Saracen et al. | 5/601 |
| 2012/0203490 A1* | 8/2012 | Sayeh et al. | 702/105 |
| 2012/0265060 A1* | 10/2012 | Ramraj et al. | 600/427 |
| 2013/0025055 A1* | 1/2013 | Saracen et al. | 5/601 |

OTHER PUBLICATIONS

Yuichiro Kamino et al. "Development of a Four-Dimensional Image-Guided Radiotherapy System with a Gimbaled X-Ray Head", Int. J. Radiation Oncology Biol. Phys., vol. 66, No. 1, pp. 271-278, 2006.

PCT International Preliminary Report on Patentability, PCT/US2007/021653 filed Oct. 9, 2007, mailed May 14, 2009.

First Notification of Office Action, Application No. 200780044846.3, date of issue Aug. 19, 2010.

* cited by examiner

COLLIMATOR CHANGER

TECHNICAL FIELD

This invention relates to the field of radiation treatment and in particular, an apparatus and a method for changing collimators in a radiation treatment system.

BACKGROUND

Some of the clinical requirements of designing a radiosurgical treatment system include providing: a) a highly precise beam delivery to targets located throughout the body, b) a highly conformal dose distribution, c) the ability to irradiate both small and/or large complex shaped lesion. To do this, the system uses a combination of beam positions whose relative weights, or dose contributions, have been scaled to volumetrically shape the dose accordingly. One or more collimators can be selected to give the beams the diameters required to achieve the desired clinical result. Current radiation treatment surgery equipment such as the CYBERKNIFE® radiosurgery system, manufactured by Accuray™ Incorporated, USA relies on a set of 12 circular, fixed size secondary collimators to reduce the beam to the size required by the treatment planning algorithm. Currently changing of these collimators is accomplished manually by hand.

FIGS. 9 and 10 illustrate the conventional process of changing collimators manually. FIG. 9 shows a locking nut 901 being removed by unscrewing the locking nut and releasing the collimator. Subsequently, the collimator may be replaced by another collimator by screwing the locking nut. Changing collimators with this version of the CYBERKNIFE® radiosurgery system, manufactured by Accuray™ Incorporated, USA, the locking nut 901 has to be rotated by multiple turns of the hand to release the collimator from off the end of a Linear Accelerator (LINAC). FIG. 10 illustrates the collimator released from a collimator housing during a manual process of changing a collimator.

One conventional process for manually changing the collimators includes the following operations. First, the operator removes the locking nut 901 by unscrewing it from the collimator housing. Next, the operator, using his/her hand, supports the collimator from the bottom. Next, the operator releases a retaining pin to release the collimator from the collimator housing to the operator's hand. Next, the operator selects a different collimator and inserts the different collimator into the collimator housing until the retaining pin clicks. Lastly, the operator replaces the locking nut 901 by screwing the locking nut 901 to the collimator housing. In this conventional process, the locking nut 901 has to be turned multiple turns to be removed from the end of the LINAC.

BRIEF DESCRIPTION OF THE DRAWINGS

The present invention is illustrated by way of example, and not by way of limitation, in the figures of the accompanying drawings.

DETAILED DESCRIPTION

Figure 1:
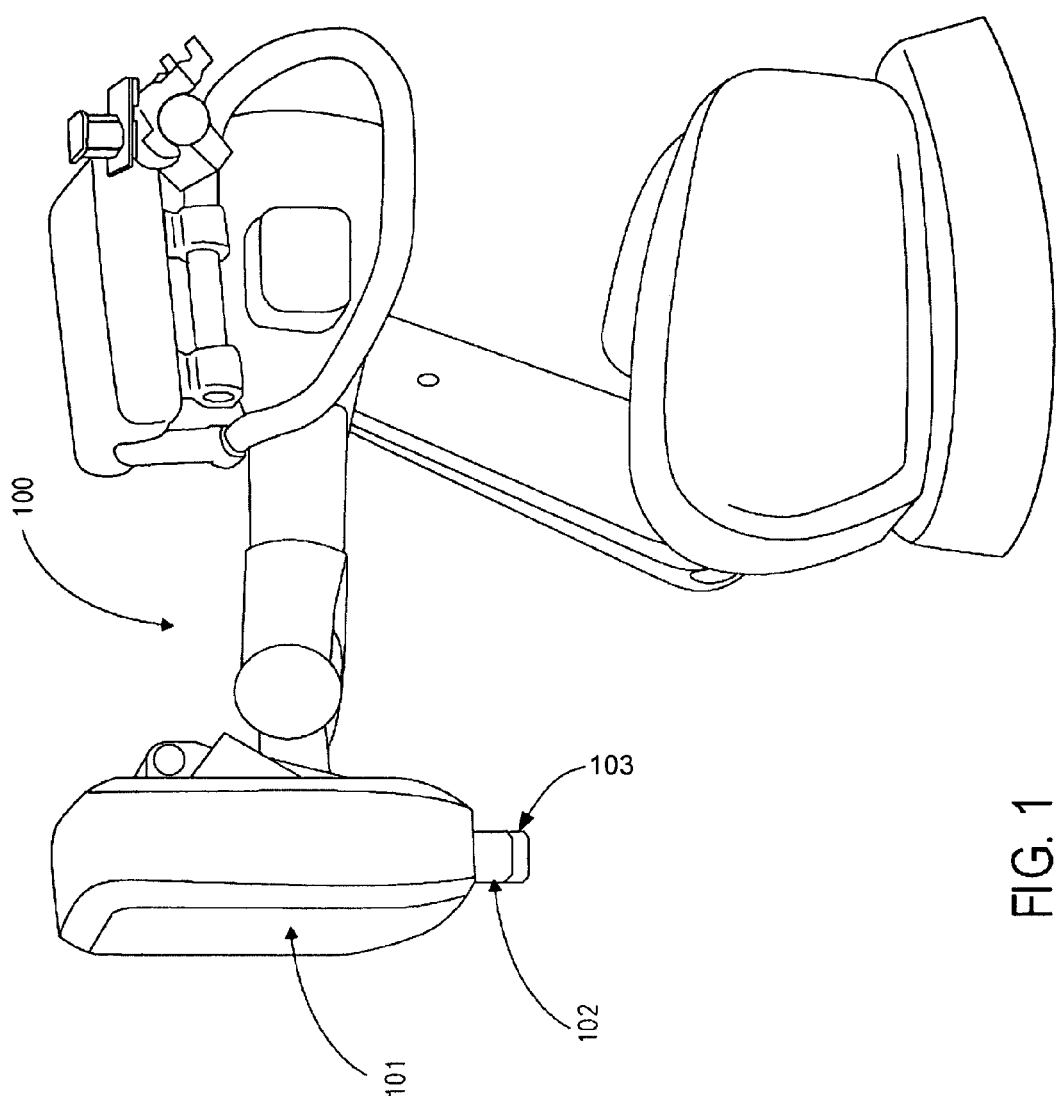
FIG. 1 illustrates one embodiment of a radiation treatment robot and an automatic collimator changer.

A method and apparatus for changing collimators in a radiation treatment system is described. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

As described in greater detail below, the embodiments described herein include an automatic collimator changer for use in radiation treatment system. The automatic collimator changer may include a collimator housing coupled to the linear accelerator of the radiation treatment system. The automatic collimator changer may also include a retention mechanism that is configured to secure a collimator in the collimator housing. The collimator housing and the retention mechanism are positioned using movements of the linear accelerator to automatically change the collimators, in place of the operator manually changing the collimators as done conventionally. Alternatively, the automatic collimator changer includes a tool changer that is removably coupled to the linear accelerator and is configured to automatically change the collimators. Similarly, the tool changer is positioned using movements of the linear accelerator to automatically change the collimators.

The automatic collimator changer may have at least one of a primary and a secondary retention mechanism coupled to the collimator housing to secure a collimator in the collimator housing. The primary and secondary retention mechanisms may be disposed both at the front end, both at the back end, or one at the front end and one at the back end. Alternatively, the automatic collimator changer may have a single retention mechanism. The single retention mechanism may be disposed at the front end of the collimator (i.e., the end at which the beam exists the collimator) of the collimator housing. Alternatively, the retention mechanism may be disposed at the back end (i.e., the end at which the beam enters the collimator) of the collimator housing.

The embodiments described herein may provide an automatic means for changing collimators. The embodiments described herein rely on the radiation treatment robot (e.g., robotic arm coupled to a LINAC) to accomplish changing of the collimators, instead of relying on an operator to manual switch the collimators as done conventionally. These embodiments may allow for a potential reduction of total radiation delivered to a target, by using multiple, different-sized collimators for each treatment plan. In addition, these embodiments may decrease the amount of operator involvement in changing the collimator, such as by eliminating the manual changing of multiple collimators. By reducing the amount of operator involvement, the treatment may be delivered according to a treatment plan without interruption of the operator entering the treatment room. These embodiments may also provide an integrated storage of collimators. The embodiments described herein may provide positional repeatability, meaning the collimator may be positioned in a repeatable position every time. By eliminating operator involvement in securing the collimator, the automatic process described herein may provide a more repeatable process than the conventional manual process, especially if more than one human operator performs the changing of the collimator. Further, in some embodiments, no extra signal or power cables are added to the radiation treatment robot to support these embodiments in existing radiation treatment systems. In other embodiments, there are no changes to the existing collimators and the LINAC, and there may be minimal changes to the contact detection sensor that is disposed on the front side of the collimator housing, which houses the collimator.

The system may be implemented using hardware and software components such as the ones described below. The hardware may include two functional components having functionality related hardware and a safety related hardware. The functionality related hardware may include a tool tray to hold collimators when not being used by the radiation treatment system. Also, the tool tray may have a means for disengaging a lock pin (also referred to as a lever). A collimator collar may secure the collimator in a collimator housing associated with the radiation treatment system. The functionality related hardware may further include a contact detection sensor and/or light sensitive sensors for calibrating the position of the tool tray in the radiation treatment robot frame. The safety related hardware may include proximity switches in the collimator housing to indicate presence or absence of a collimator. These proximity switches are also referred to as presence-absence sensors. A proximity switch may also be positioned under the tool tray to detect contact between the linear accelerator and the tool tray. Further, the tool tray may be designed with stress points to allow the tool tray to break before causing damage to the linear accelerator in case of contact between the linear accelerator and the tool tray. The safety related hardware may also include at least one proximity switch on the collimator housing associated with the linear accelerator, to indicate proper locking of the collimator collar.

The safety related measures are put in place so as to mitigate hazards, such as, for example, the collimator falling on the patient. This hazard may be mitigated by the check switch on the position of the collimator collar. In one embodiment, the check switch is a proximity switch, placed at the end of the turn of the collimator collar to ensure that the collimator collar is positioned correctly. This mechanical configuration ensures that the position of the proximity switch is such that once tripped, the collimator collar is tight and in a fully secured position. Another hazard example may be with the linear accelerator colliding with a patient. This hazard includes may include a three-stage mitigation; 1) light sensors to check the position of the tray, 2) proximity switches to indicate contact with the tray and 3) breakaway stress points to prevent damage to the linear accelerator. The same three stage mitigation may be applied to avoid the hazard of the radiation treatment robot colliding with the tool tray.

In alternative embodiments, software may integrate all functionality and safety related hardware into the radiation treatment robot such as the CYBERKNIFE® radiosurgery system manufactured by Accuray™ Incorporated, USA. The software may ideally provide an abstraction layer so that the rest of the system does not need to know detailed information about the state or functionality of the tool tray.

FIG. 1 illustrates one embodiment of a radiation treatment robot 100 and an automatic collimator changer 103. In one embodiment, all of the movement associated with the collimator changer may be provided by the radiation treatment robot 100 with no additional actuation required. The motion may be mechanical and such motion may rely on certain contours to trigger certain spring mechanism in the radiation treatment robot 100. In one embodiment, the articulation capability of the radiation treatment robot 100 is used to pick up the collimators 401 from the tool tray 400 and drop off the collimators 401 in the tool tray 400. The dropping off and picking up of the collimators 401 may be done by mere movement of the radiation treatment robot 100. In some embodiments, a user may program the radiation treatment robot 100 to be positioned in the right spot for picking up and dropping off collimators 401. In the embodiment illustrated in FIG. 1, the radiation treatment robot 100 (or radiation treatment device) includes a linear accelerator (LINAC) 101 which is coupled the automatic collimator changer 103.

The automatic collimator changer 103 includes the collimator housing 102. The automatic collimator changer 103 may also include one or more retention mechanisms (not illustrated in FIG. 1) that are coupled to the collimator housing 102 to engage or disengage a collimator in the collimator housing 102. Alternatively, the automatic collimator changer 103 includes a tool changer (e.g., pneumatic tool changer). The tool changer may be configured to drop off or pick up collimators to be secured to the collimator housing 102. The tool changer may also be configured to pick up a collimator housing that includes one or more retention mechanisms, as described herein.

The movement of the automatic collimator changer 103 may be provided by the radiation treatment robot 100, and the automatic collimator changer 103 may require no additional actuation by the radiation treatment robot 100 in some embodiments (e.g., embodiments that do not use a tool changer). The automatic collimator changer 103 and the movement of the radiation treatment robot 100 may be configured to automatically change the collimator in the collimator housing 102. Alternatively, the radiation treatment systems may include other types of radiation treatment robots than the radiation treatment robot 100 and/or other types of radiation treatment delivery devices that include at least one collimator.

In one embodiment, the automatic collimator changer 103 includes only passive mechanical components, such as one or more retention mechanisms coupled to the collimator housing 102 to secure and release the collimator from the collimator housing 102. The automatic collimator changer 103 in these embodiments rely on the motion of the radiation treatment robot 100 to position the collimator housing 102 such that the retention mechanisms are engaged and disengaged to pick up and drop off the collimators. Since these components are passive mechanical components, no additional power is required to operate the automatic collimator changer.

In another embodiment, the automatic collimator changer 103 may include active electronic components (e.g., components to actuate a tool changer to pick up or drop off the collimators) that operate in conjunction with the mechanical components, such as the collimator and the collimator housing. Similarly, the movement of the radiation treatment robot 100 can be used to position the automatic collimator changer 103, having active electronic components (e.g., tool changer) to pick up and drop off the collimators. Alternatively, the automatic collimator changer 103 may include both passive and active components for changing the collimators.

Figure 2:
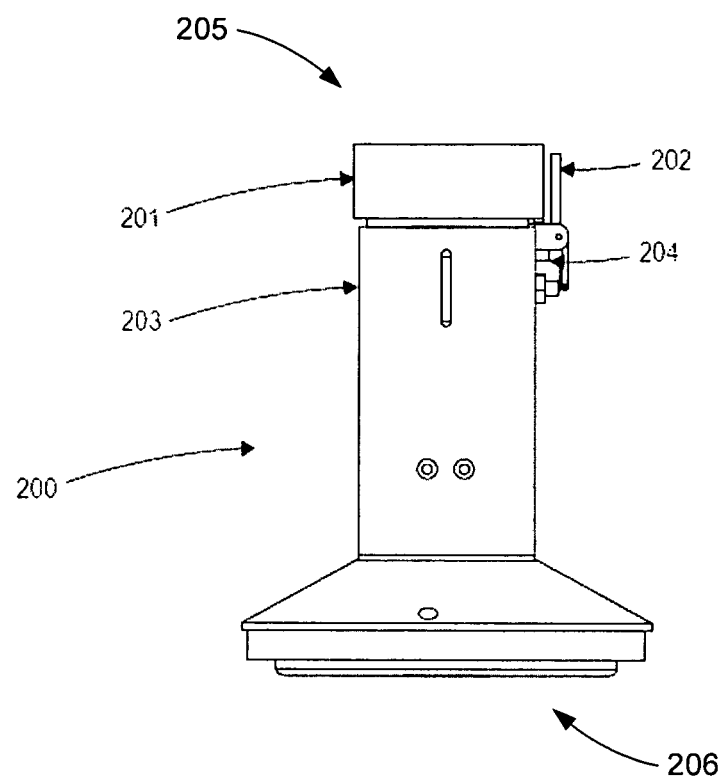
FIG. 2 illustrates one embodiment of a collimator housing of a radiation treatment robot.

FIG. 2 illustrates one embodiment of a collimator housing 200. The collimator housing 200 may be coupled to the linear accelerator 101. In one embodiment, the collimator housing 200 includes a primary retention mechanism 201 and a secondary retention mechanism 202. The primary retention mechanism 201 and the secondary retention mechanism 202 are coupled to the collimator housing 200. The primary retention mechanism 201 and the secondary retention mechanism 202 are both configured to secure a collimator 401 in the collimator housing 200. In one embodiment, the primary retention mechanism 201 provides a positive locking force against the collimator. In one embodiment, the primary retention mechanism 201 is a nut, such as a locking nut. In one embodiment, the locking nut includes a stop on the locking nut so that the locking not cannot turn past the stop. Alternatively, the locking nut may not include a stop. In another embodiment, a sensor, such as the proximity switch 204 described below, may be provided to indicate that the locking nut is secured to the collimator housing. In another embodiment, the secondary retention mechanism 202 is a lock pin coupled to the collimator housing 200. Alternatively, the secondary mechanism may be a locking mechanism, a screwing mechanism, or the like.

In another embodiment, the primary retention mechanism 201 may be a collimator collar. The collimator collar may be configured to positively lock on to the collimator housing 200. Such positive locking may be accomplished by a quarter turn of the linear accelerator 101. Positive locking may include applying a positive force to release a lock, without relying on friction or a spring. Without the positive force being applied, the primary retention mechanism remains locked. The collimator collar 201 may also be referred to as a "quarter-turn" locking mechanism. The locking nut 901 may have a hand-tightening torque requirement, such as that an average operator can remove and replace the locking nut using one hand. It will be appreciated that the primary retention mechanism 201 may be coupled to the collimator housing via a screw mechanism. The screw mechanism may be achieved by threading the collimator collar 201 and screwing the primary retention mechanism 201 on to the collimator housing 200. In one embodiment, the primary retention mechanism 201 is coupled to the collimator housing by turning the primary retention mechanism 201 approximately 45 degrees to secure (e.g., lock or screw) the collimator to the collimator housing 200. Alternatively, the primary retention mechanism 201 may be turned more or less degrees than 45 degrees, such as 90 degrees. In another embodiment, the primary retention mechanism 201 is a carousel coupled to the housing 200, acting as a shield to secure the collimator in the collimator housing 200. Alternatively, the primary retention mechanism 201 may be other types of retention mechanisms known by those of ordinary skill in the art, such as locking mechanisms, screwing mechanisms, pin mechanisms, or the like. For example, in another embodiment, the retention mechanism may be threads on the collimator (e.g., modifying a tungsten collimator so that the outside surface has a coarse spinal thread), and corresponding mating threads on the collimator housing. The movement of the radiation treatment robot 100 caused the collimator threading to engage mating threads on the inside surface of the collimator housing. In this embodiment, the collimator operates as a thread screw and the collimator housing operates as the matching nut.

In another embodiment, the collimator housing 200 includes a single retention mechanism, such as one of the primary or secondary retention mechanisms described above. In one embodiment, for example, the single retention mechanism is disposed on a front end of the collimator housing. The single retention mechanism may be threading on the collimator to engage with threading in the collimator housing. In another embodiment, a contact sensor is disposed at the front end of the collimator housing with the single retention mechanism. The contact sensor may include a cavity disposed on the periphery of a housing of the contact sensor, and the retention mechanism is disposed in the cavity of the contact sensor. By disposing the retention mechanism in the cavity of the housing of the contact sensor, the contact sensor is not activated when the retention mechanism is engage or disengaged when interacting with the collimator receptacles. Alternatively, the retention mechanism and the contact sensor are disposed at the front end of the collimator housing in other configurations.

In one embodiment, the collimator housing 200 includes at least one proximity switch 204. The proximity switch 204 is coupled to the collimator housing 200 and is configured to indicate when the collimator is securely coupled to the collimator housing 200. In one embodiment, the proximity switch 204 is used to detect the presence of the primary retention mechanism 201 (e.g., collimator collar or nut). In one embodiment, the proximity switch 204 is an electromechanical switch. Alternatively, the proximity switch may be other types of switches known by those of ordinary skill in the art, such as an electrical sensor switch.

In one embodiment, the primary and secondary retention mechanisms 201 and 202 are disposed at the front end 205 of the collimator housing 200. Although illustrated in FIG. 2 as being disposed both at the front end 205, the primary and secondary retention mechanism may also be disposed both at the back end 206, or one at the front end 205 and one at the back end 206. Alternatively, the collimator housing may have a single retention mechanism (e.g., collimator collar or nut). The single retention mechanism may be disposed at the front end 205 of the collimator housing. Alternatively, the retention mechanism may be disposed at the back end 206 of the collimator housing.

Figure 3:
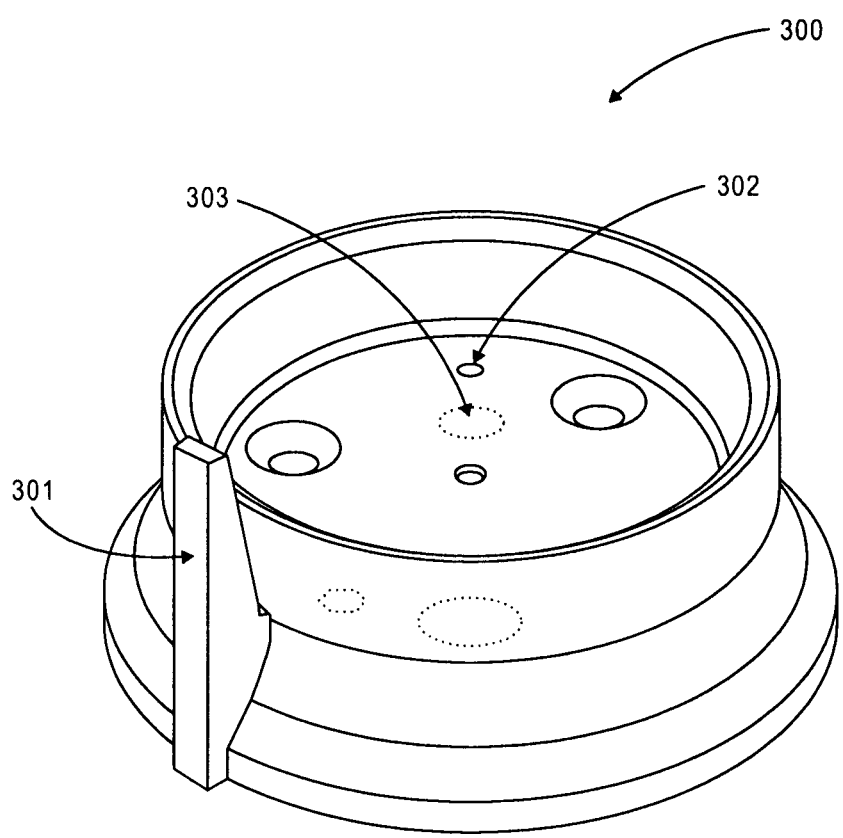
FIG. 3 illustrates one embodiment of a collimator receptacle associated with a tool tray of a system for changing collimators.

FIG. 3 illustrates an embodiment of a collimator receptacle 300. In an embodiment, a tool tray 400 includes one or more collimator receptacles that each house one collimator 401. The collimator receptacle 300 may include a guide mechanism 301. The guide mechanism 301 may be configured to engage a retaining pin of the collimator housing as it is lowered. The guide mechanism 301 may pull the pin, freeing the collimator 401 from the collimator housing 200. In another embodiment, the guide mechanism 301 includes a ramp to actuate the lock pin (e.g., secondary retention mechanism 202) to release the collimator 401 into the empty collimator receptacle 300. The guide mechanism 301 may be coupled to the collimator receptacle 300 to disengage the lock pin when the radiation treatment robot 100 moves toward the collimator receptacle 300 to release the collimator 401 from the collimator housing 200 to the collimator receptacle 300.

In another embodiment, the collimator receptacle 300 may have sensors 302 to detect a presence or an absence of the collimator 401 in the collimator receptacle 300. The collimator receptacle 300 may also have a directional sensor 303 for calibrating the position of the collimator 401 in the collimator receptacle 300 with respect to the radiation treatment robot 100.

It should be noted that although FIG. 3 illustrates a collimator receptacle having one or more sensors, such as sensor 302 and direction sensor 303, the collimator receptacle may be implemented without the sensor 302 and/or the direction sensor 303.

Figure 4:
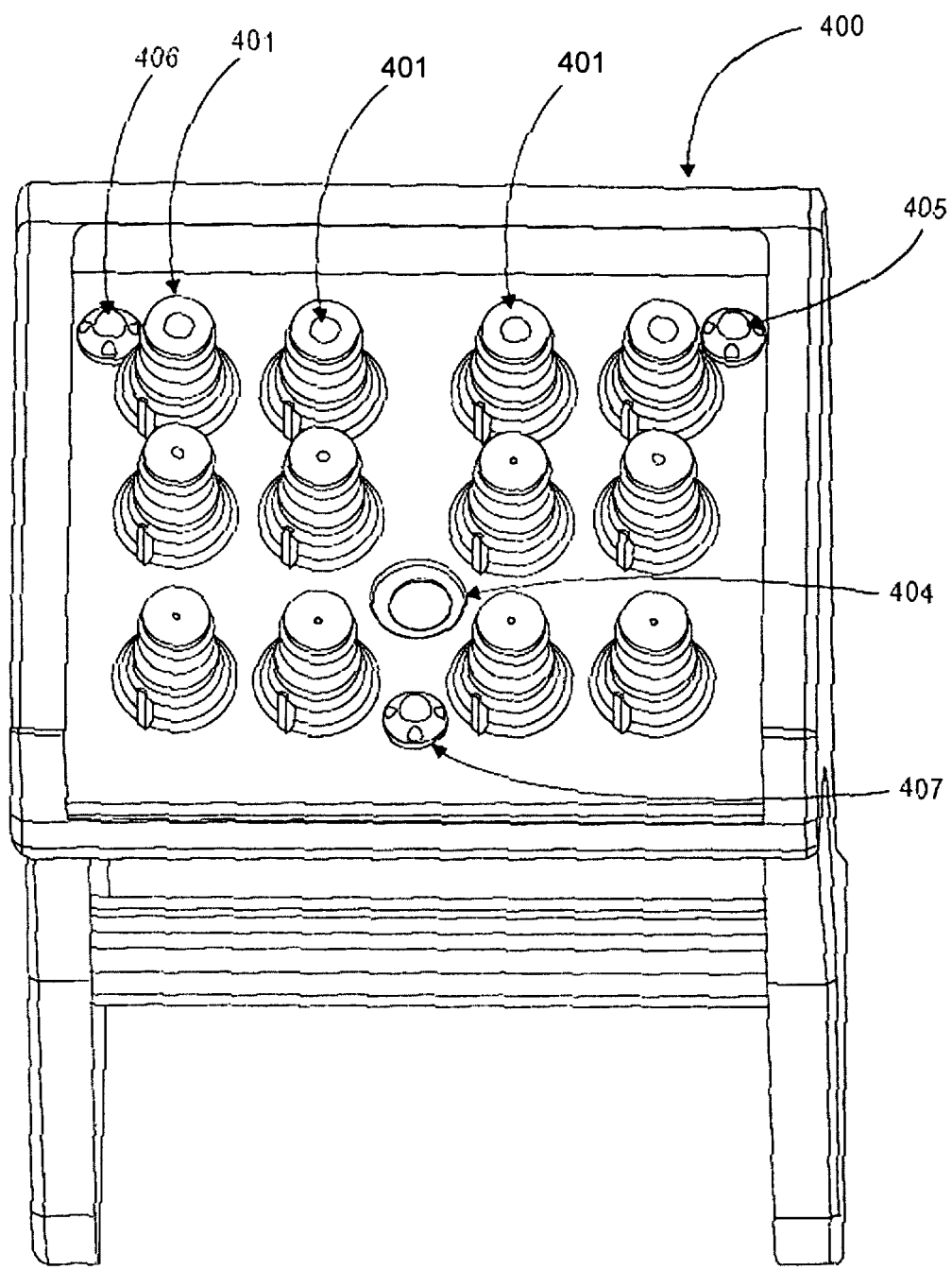
FIG. 4 illustrates one embodiment of a tool tray of a system for changing collimators.

FIG. 4 illustrates an embodiment of a tool tray 400. In this embodiment, the tool tray 400 includes multiple collimator receptacles 300 for holding multiple collimators 401. In one embodiment, the tool tray 400 includes a set of twelve collimator receptacles 300 for holding a set of twelve circular, fixed-size collimators 401. Alternatively, the tool tray 400 may include one or more collimator receptacles 300.

In one embodiment, each collimator receptacle is a keyed cavity 404 that is configured to hold a collimator collar (e.g., primary retention mechanism 201). Alternatively, the collimator receptacles may not be keyed.

In one embodiment, the tool tray 400 may includes at least one light sensitive sensor, for example, three light sensitive sensors 405, 406, and 407, coupled to the tool tray 400 for calibrating the position of the tool tray 400 in the radiation treatment robot 100 frame. For example, the light sensitive sensors may be used to make sure that the collimator is deposited in the center of the collimator receptacle. As described above, the linear accelerator 101 generates one or more radiation beams. These radiation beams may be detected by the three light sensitive sensors 405, 406, and 407. The sensors 405, 406, and 407, may report to the controller of the linear accelerator to calibrate the position of the tool tray 400 in the frame of the linear accelerator. This calibration allows the radiation treatment robot to position the collimator to engage with the proper collimator receptacle, and in the proper position within the collimator receptacle. In one embodiment, at least one sensor is placed in each of the collimator receptacles. Alternatively, more or less light sensitive sensors may be used.

In another embodiment, the tool tray includes one or more fixed, quick-check sensors coupled to the tool tray 400. The quick-check sensor may be a light sensitive sensor that is used to determine that the linear accelerator is correctly positioned over the tool tray, as a final check before engaging or disengaging collimators in the collimator receptacles of the tool tray. Multiple light sensitive sensors may be used in registering the position of the tray table in the frame of the linear accelerator, and one sensor may be used to quickly check the position of the tool tray without performing the registration process using multiple light sensitive sensors. In another embodiment, the tool tray 400 includes a second set of at least one proximity switch to detect contact between the radiation treatment robot 100 and the tool tray 400. This second set of at least one proximity switch may be positioned under the tool tray 400. In an embodiment, the tool tray 400 includes stress points in the tool tray 400 to allow the tool tray 400 to break before causing damage to the radiation treatment robot 100 in the event of contact between the tool tray 400 and the radiation treatment robot 100. Alternatively, the tool tray 400 may include light sensitive sensors, proximity sensors, stress points, or any combination thereof.

Figure 5:
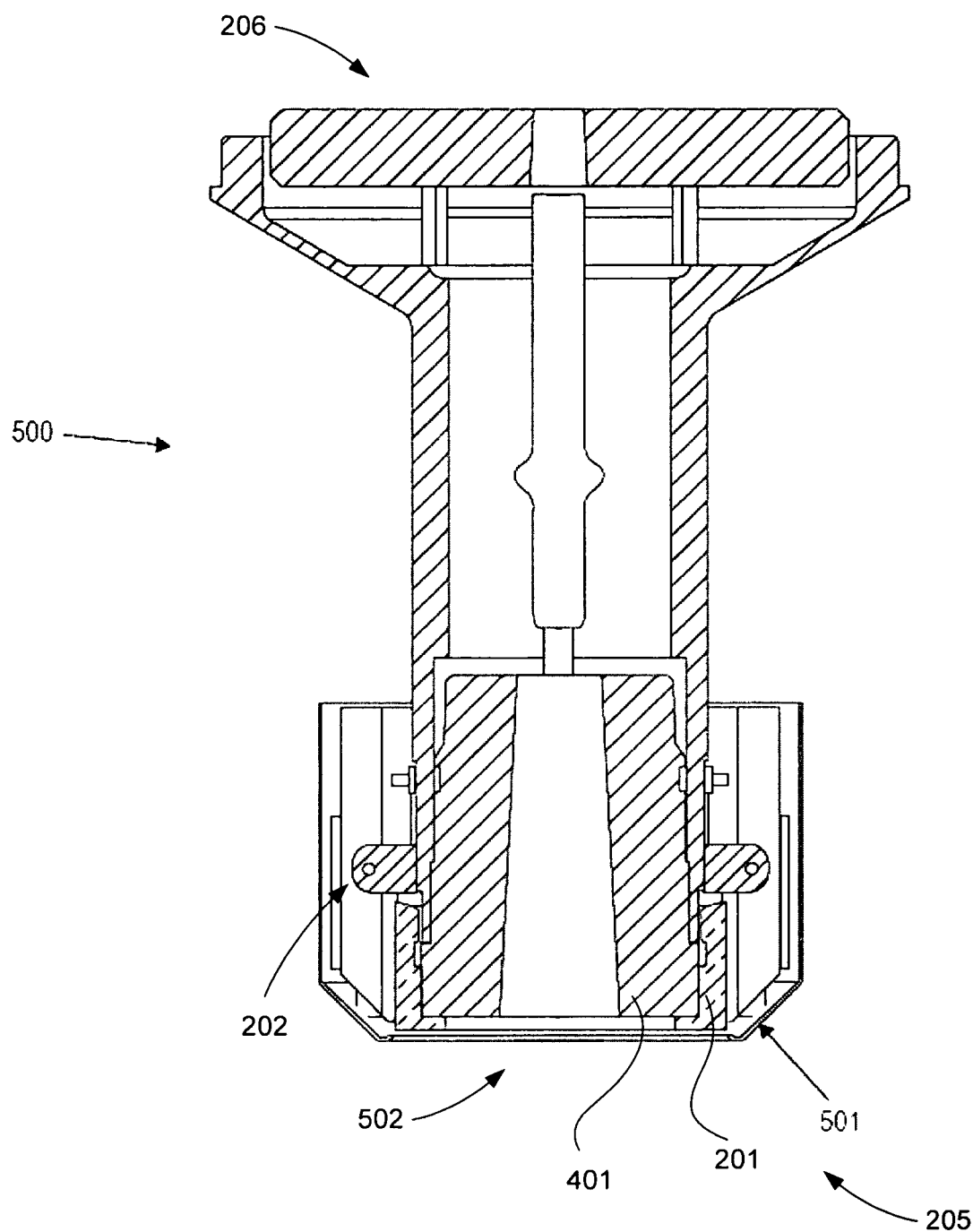
FIG. 5 illustrates one embodiment of a collimator housing of a radiation treatment robot.

FIG. 5 is an illustration of a collimator housing 500. In the embodiment illustrated in FIG. 5, the collimator housing 500 is coupled to at least one contact sensor 501 to detect contact between the radiation treatment robot 100 and the tool tray 400 and/or contact between the radiation treatment robot 100 and a patient. Alternatively, the contact sensor may be used to detect contact with other objects in the treatment room.

In this embodiment, the contact sensor 501 is disposed on the front end 205 of the collimator housing 500. In one embodiment, the contact sensor 501 includes a cavity 502 disposed on the periphery of the contact sensor 501. The primary retention mechanism 201, for example, a nut or a collimator collar, is disposed in the cavity 502 of the contact sensor 501. In another embodiment, the secondary retention mechanism 202 is disposed in the cavity 502 of the contact sensor 501. Alternatively, the contact sensor 501 may be implemented on the collimator housing 500 in other configurations that permit the automatic functionality of the primary retention mechanism 201 (or the secondary retention mechanism 202) without operator intervention.

Figure 6:
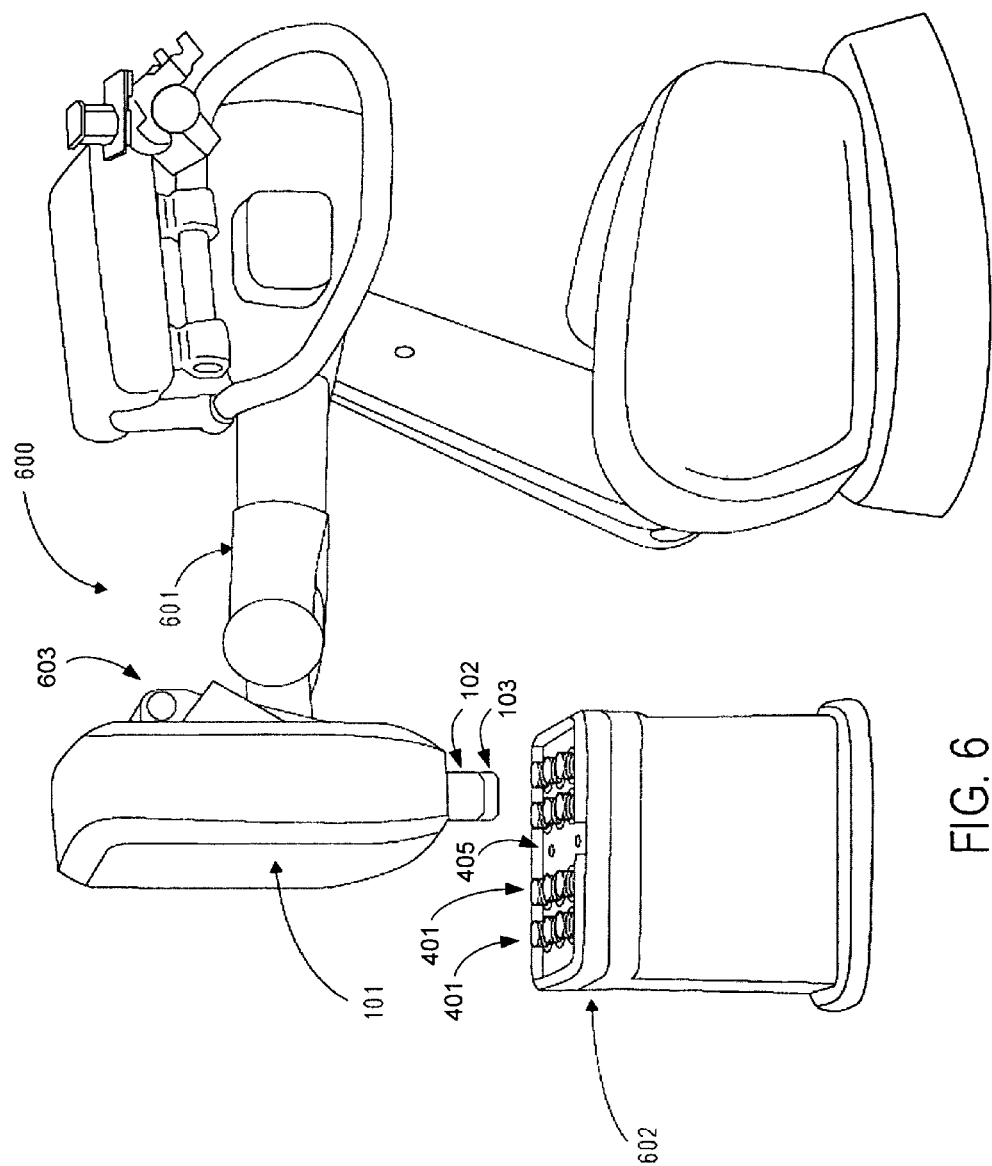
FIG. 6 illustrates one embodiment of a system for changing collimators.

FIG. 6 is an illustration of an embodiment of a system for changing collimators 600. The system 600 includes a radiation treatment robot 601 and a tool tray 602 placed within the reach of the radiation treatment robot 601. The radiation treatment robot 601 is coupled to the linear accelerator 101 via back plate 603. The system 600 includes twelve collimators 401. These collimators may be twelve circular, fixed-size collimators. The tool tray 602 includes twelve corresponding collimator receptacle 300. The radiation treatment robot 601 is coupled to a collimator housing, such as collimator housing 102, collimator housing 500, or collimator housing 200. The radiation treatment robot 601 and the automatic collimator changer 103 may be configured to switch one of the twelve collimators 401 from a collimator receptacle 300, associated with the tool tray 602, to a collimator housing 500. The radiation treatment robot 601 and the automatic collimator changer 103 may also be configured to switch one of the twelve collimators 401 from the collimator housing 500 to a corresponding collimator receptacle 300 in the tool tray 602. The automatic collimator changer 103 may have a primary retention mechanism and/or a secondary retention mechanism. In one embodiment, the primary retention mechanism is a collimator collar 201. The primary retention mechanism is coupled to the collimator housing 500. The collimator collar 201 may engage the collimator receptacle 300 of the tool tray 602, for example, using via a locking mechanism that may adopt positive style locking. The radiation treatment robot 601 may be turned approximately a quarter-turn to achieve the positive locking between the collimator collar 201 and the collimator housing 500. When in the lock position, a collimator 401 is secured in the collimator housing 500. Alternatively, the radiation treatment robot 601 is not turned, and a pneumatic tool changer may be used for the automatic collimator changer 103 to secure the collimator 401 in the collimator housing. In one embodiment, the presence and/or absence of the collimator 401 may be detected using one or more sensors. The existing collimators 401 may be arranged in a tool tray 602 and placed within the reach of the radiation treatment robot 601. The collimator collar 201, which may be brass, may be deposited in one of the collimator receptacles 300 of the tool tray 602. In one embodiment, the collimator receptacle 300 is a keyed cavity 404, having a quarter-turn locking mechanism.

Figure 7:
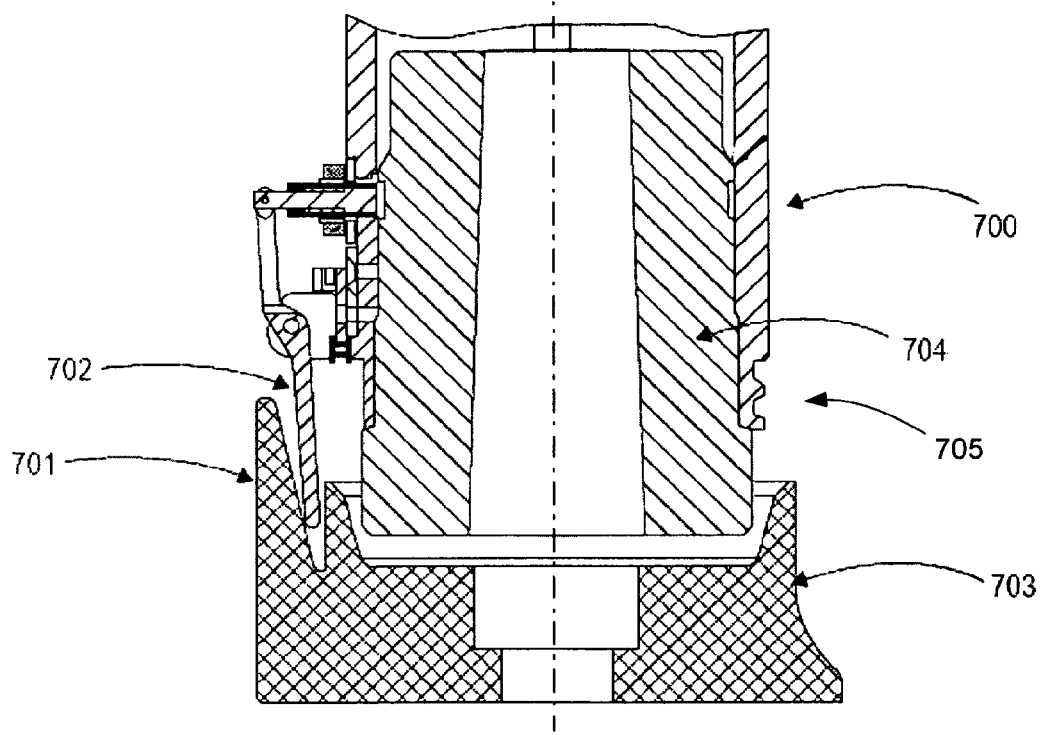
FIG. 7 illustrates an embodiment of a collimator housing of a radiation treatment robot engaging a collimator receptacle.

FIG. 7 illustrates an embodiment where the guide mechanism 701 associated with the collimator receptacle 703 disengages the lock pin 702 of the collimator housing 700. The collimator housing 700 houses the collimator 704. Collimator 704 may be similar to the collimators 401 described above. In this embodiment, the lock pin 702 of the collimator housing 700 makes contact with the guide mechanism 701 of the collimator receptacle 703. In one embodiment, the guide mechanism 701 has a ramp that actuates the lock pin 702 and disengages the lock pin 702, releasing the collimator 704 from the collimator housing 700 to be deposited in the collimator receptacle 703.

FIG. 7 also illustrates threading 705 of the collimator housing 500 wherein a primary retention mechanism 201 (e.g., nut or collimator collar) may be screwed onto the collimator housing.

Figure 8:
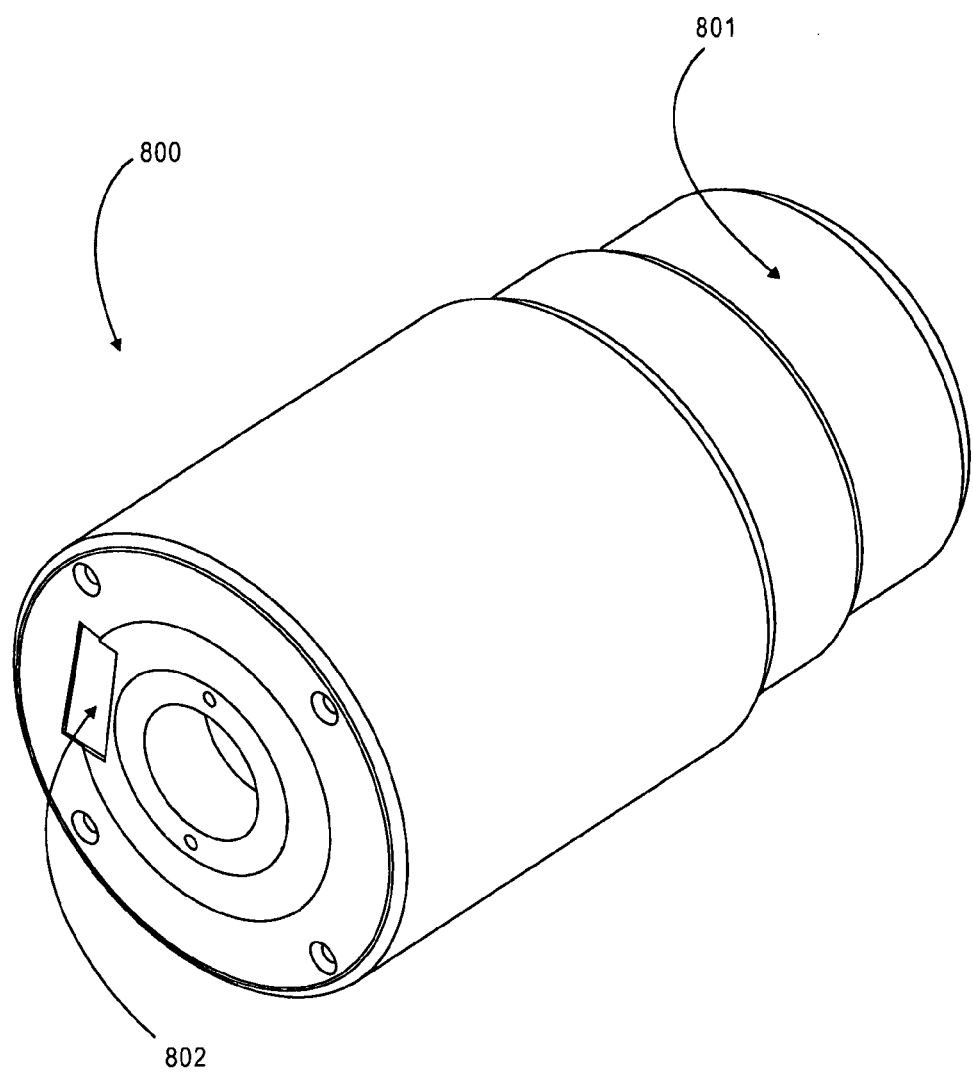
FIG. 8 illustrates an embodiment of a tool changer.
Figure 9:
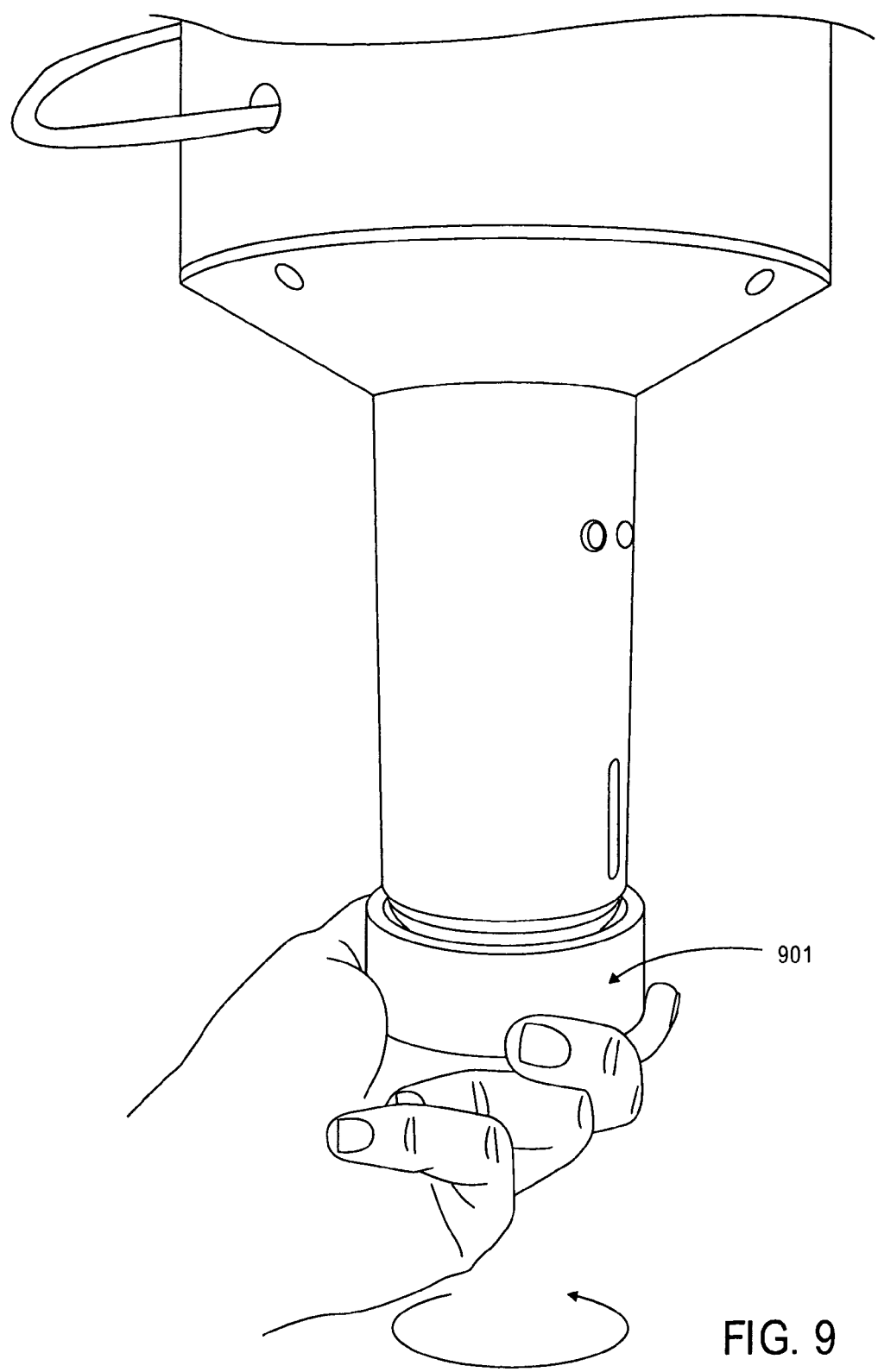
FIG. 9 illustrates a manual process of changing a collimator.
Figure 10:
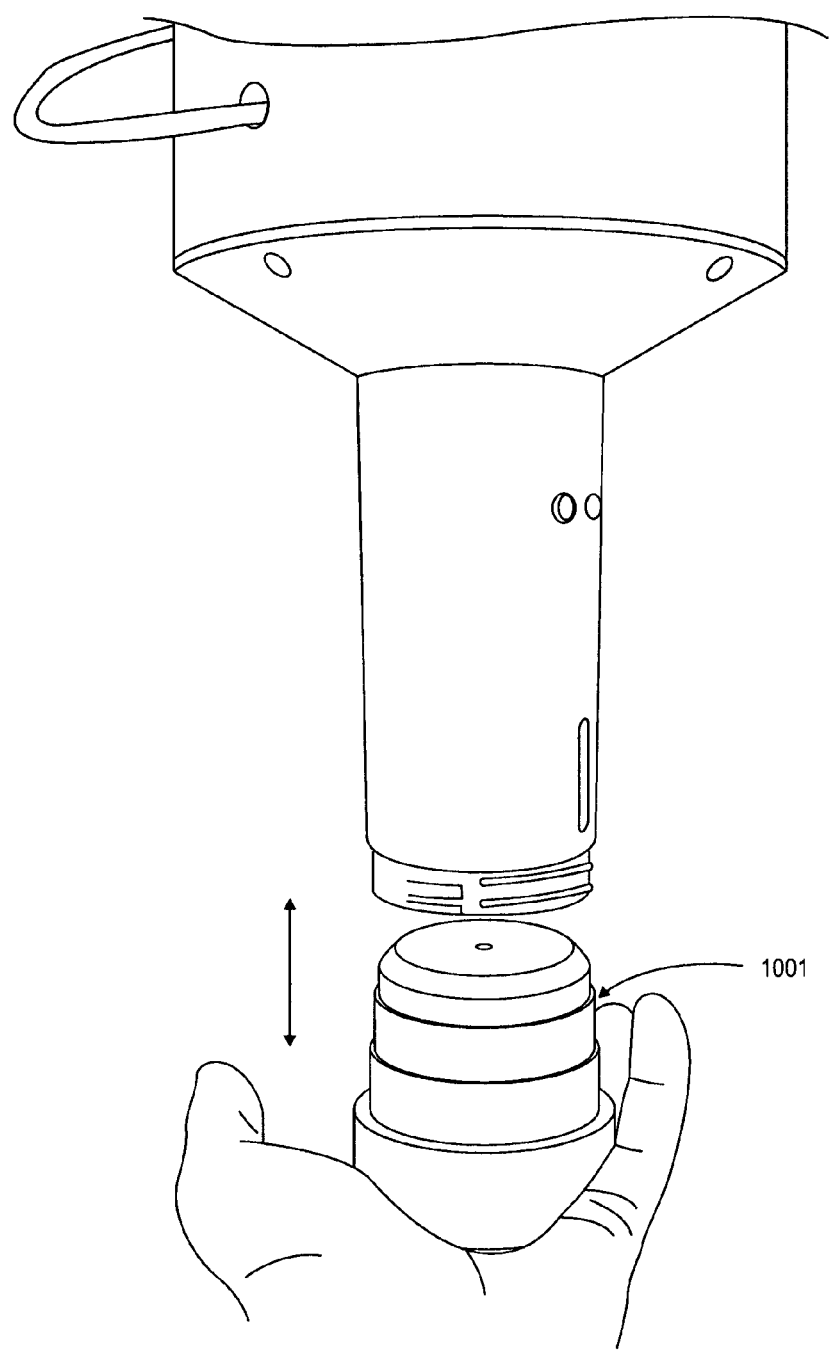
FIG. 10 illustrates a collimator released from a collimator housing during a manual process of changing a collimator.

FIG. 8 illustrates an embodiment of a tool changer. The tool changer 800 may be used as an automatic collimator changer to change one or more collimators 401 of a radiation treatment system. In one embodiment, the tool changer 800 is a pneumatic tool changer. A pneumatic tool changer may be fairly small in size, usually between approximately 50 millimeter diameter and approximately 25 millimeter height and do not require extra space. Alternatively, other tool changers known by those of ordinary skill in the art may be used to engage and disengage one or more collimators in the collimator housing.

In another embodiment, the tool changer 800 is configured to pick up a housing of a variable-sized collimator. The variable-sized collimator may be a collimator with a programmable size. The housing, the variable-sized collimator, and other necessary electromechanical components may be integrated into one self-contained module. The connecting interface of this module to the linear accelerator may be similar to the connecting interface of the collimator housing, described herein, that is used for fixed-size collimators. In another embodiment, the tool changer 800 is configured to pick up a collimator housing that is used for picking up one or more fixed size collimators. In one embodiment, the tool changer 800 is coupled to a housing of a primary collimator and the housing of the primary collimator is coupled to the linear accelerator.

In one embodiment, the tool changer includes active elements, such as sensor 801, air pressure, etc. Alternatively, other active elements may be included. In one embodiment, the active elements include one or more actuators to engage or disengage the collimators. In another embodiment, the active elements includes a motor or some other actuation in the tool tray to remove the collimator collar from the collimator receptacle, instead of the radiation treatment robot 100 moving the whole linear accelerator to remove the collimator collar. In another embodiment, the active elements include a drive mechanism in a rotating or translating carrousel, which houses multiple fixed-size collimators. The drive mechanism in the carrousel may bring the desired collimator into the path of the beam of the linear accelerator to provide the necessary collimation. These active elements may be located in various locations, such as on the linear accelerator 101, on the robotic arm 601, or alternatively, on the tool tray 602. In one embodiment, the mounting the tool changer 800 is accomplished by strengthening the linear accelerator back plate (e.g., back plate 603 illustrated in FIG. 6). These designs may have one or more tool changer modules positioned around the collimator 401 and the mounting of the tool changers 800 may be accomplished by strengthening the linear accelerator back plate. The back plate is coupled between the robotic arm 601 and the linear accelerator 101. Also, each collimator housing may be mounted in a common interface plate that matches up with the tool changer configuration. The common interface plate may reside on the collimator or on a housing of the collimator in a design that includes both a primary and secondary collimator, there may be an interfacing plate on the primary collimator or the primary collimator housing, which mates with the tool changer. Alternatively, other configurations known by those of ordinary skill in the art may be used, such as a decoupled pronged mount, or the like.

When the active elements of the pneumatic tool changer are implemented on the linear accelerator, the tool changer is actuated by supplying pneumatic pressure, which releases the collimator 401 in the collimator receptacle. To engage a collimator in the collimator receptacle, air pressure may be removed from the tool changer. In this embodiment, the air-supply line (also known as air-pressure line) is supplied to the linear accelerator. In this embodiment, all the actuation and signal lines may be routed through the current cabling of the linear accelerator 101, and through, for example, an electrical feed 802 of the tool changer 800.

In another embodiment, an air-supply line is connected to the active elements of the tool changer that are mounted on the robotic arm 601. In this embodiment, the active elements mounted to the robotic arm 601 are in proximity of the tool tray. In this embodiment, the tool changer is actuated by supplying pneumatic pressure to release the collimator. To engage a collimator in the collimator receptacle, air pressure may be removed from the tool changer. In one embodiment, the automatic collimator changer is a pneumatic tool changer mounted to the radiation treatment robot. Instead of providing a pressurized air supply for the pneumatic tool changer from the radiation treatment robot, a quick-connect air supply may be provided at the tool tray. To engage/disengage the collimator, the radiation treatment robot positions the pneumatic tool changer in a position that the quick-connect air supply of the tool tray can be connected to the pneumatic tool changer for picking up or dropping off the collimator in the collimator receptacles of the tool tray.

Figure 11:
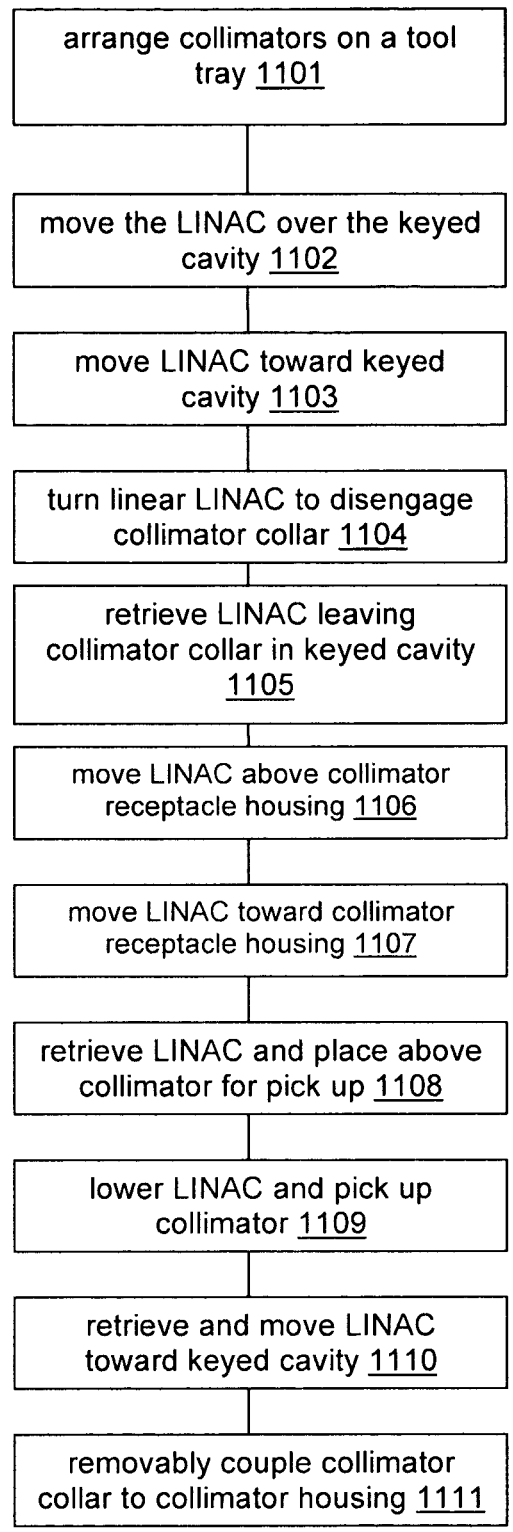
FIG. 11 is a flowchart illustrating one embodiment of a process for automatically changing collimators.

FIG. 11 is a flowchart illustrating one embodiment of the process for automatically changing collimators. The sequence of events at the time of tool exchange may include populating the tool tray 400 with the collimators 401. In a first operation 1101, the collimators are arranged on the tool tray so that the collimators are within reach of the linear accelerator 101. In starting a treatment plan, the radiation treatment system checks the required collimator size. If the correct collimator 401 is installed in the collimator housing 203, the treatment proceeds without interruption. However, if the incorrect collimator 401 is installed, the user is presented with the option to automatically change the collimator 401, to check again or to abort. Selecting the option to automatically change will start the process of changing the collimator. The rest of these operations outline the events that may happen during the collimator change. The system checks to see if the assigned keyed cavity 404 for the collimator collar 201 is empty. If the keyed cavity is not empty, the radiation treatment system may post an error and force a manual change by an operator. In a second operation of the flow chart 1100, the radiation treatment robot 100 moves the linear accelerator 101 into the assigned position where it can check the position of the tool tray 400 using the linear accelerator laser. This may be done using one or more light sensitive sensors that are mounted to the tool tray. If proper positioning cannot be ascertained, a manual change may be forced. In this operation 1102, the linear is subsequently moved over the keyed cavity 404 of the tool tray 400. In a third operation 1103, the radiation treatment robot then approaches the tool tray 400, and lowers the linear accelerator, into a keyed cavity 404 which houses the collimator collar 201. In a fourth operation 1104, the radiation treatment robot 100 then turns by a quarter turn to disengage the collimator collar 201 from the collimator housing 200 into the collimator receptacle. In a fifth operation 1105, the radiation treatment robot 100 then retrieves the LINAC from the tool tray 400, leaving the collimator collar 201 in the keyed cavity 404. In a sixth operation 1106, the LINAC is then moved above a collimator receptacle 300, where the desired collimator 401 is housed. In a seventh operation 1107, the linear accelerator is then moved toward the collimator receptacle 300. The collimator housing 200 is engaged by the guide mechanism 301 of the collimator receptacle 300 to release the collimator 401 from the collimator housing 200 to the collimator receptacle 300. To release the collimator 401 from the collimator housing 200 to the collimator receptacle 300, the guide mechanism 301 which is positioned at a slant engages the lock pin 702 of the collimator housing 700 as the collimator housing 700 is lowered toward the collimator receptacle 703. The guide mechanism 701 then pulls the lock pin 702, freeing the collimator 704 and the collimator 704 is deposited into the collimator receptacle 703. The system may check to ensure that the collimator 704 is in fact removed. In an eighth operation 1108, the linear accelerator is retrieved and positioned above the collimator 401 to be picked up. The system checks to see if the desired collimator receptacle 300 has a collimator 401 in it. In a ninth operation 1109, the collimator housing 200 is lowered to pick-up the collimator 401. Here the angle of rotation of the linear accelerator about its axis is different than the angle of rotation of the linear accelerator when dropping a collimator 704. As a result, during pick up of a collimator 401, the lock pin 202 is not engaged with the guide mechanism 301. In a tenth operation 1110, the collimator housing 200 is then retrieved and is moved toward the keyed cavity 404 where the collimator collar 201 resides. In an eleventh operation 1111, the collimator housing 200 engages the collimator collar 201 and the linear accelerator is turned quarter-turn to removably couple the collimator collar 201 to the collimator housing 200. The collimator is also secured by the lock pin 202 in the collimator housing 200. After successful exchange the radiation treatment robot may return to a perch position and continues the treatment delivery according to the treatment plan.

Figure 12:
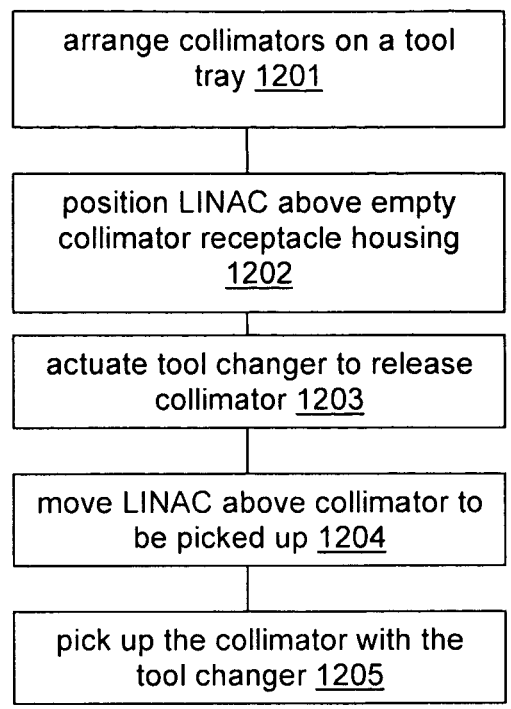
FIG. 12 is a flowchart illustrating another embodiment of a process of automatically changing collimators.

FIG. 12 is a flowchart 1200 illustrating one embodiment of the process of automatically changing collimators. In a first operation 1201, the collimators are arranged in a tool tray so that the collimators are within reach of the linear accelerator 101. In a second operation 1202, the linear accelerator 101 is positioned over the tool tray 602 above an empty collimator receptacle 300. In third operation 1203, the tool changer 800 is then actuated by supplying pneumatic pressure to release the collimator 401 from the collimator housing associated with the tool changer to the collimator receptacle 300. In a fourth operation 1204, the linear accelerator 101 is then moved above the collimator receptacle 300 containing the desired collimator 401. In a fifth operation 1205, the air pressure is removed from the tool changer 800 and the collimator 401 is picked up.

In an alternative embodiment, the system may include a mechanism for connecting the air pressure line to the tool changer 800 mounted on the radiation treatment robot 601 in the proximity of the tool tray 602. These following operations may be added to the sequence of changing the collimator 401 outlined above. The tool changer 800 is moved into position and latch to the air supply line. The air supply line is usually a flexible hose and it may be connected to the tool changer 800 throughout the change operations. After the completion of the change of collimators, the air supply line is placed in a designated slot and the supply line disconnects.

Figure 13:
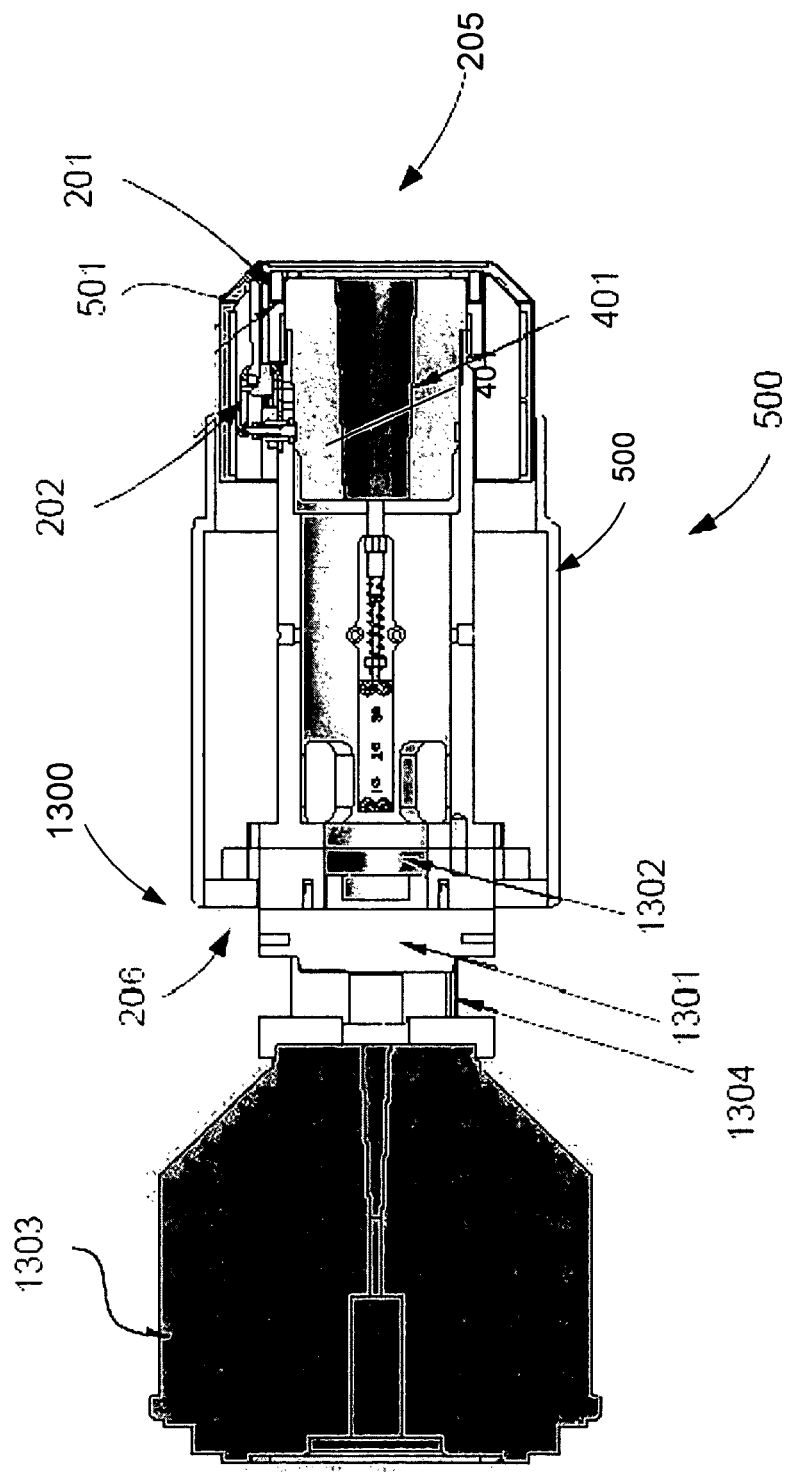
FIG. 13 illustrates one embodiment of a tool changer and a collimator housing of a second collimator.

FIG. 13 illustrates one embodiment of a tool changer and the collimator housing of a second collimator. Tool changer 1301 may be similar to the tool changer 800 described above with respect to FIG. 8. The tool changer 1301 is coupled to a collimator housing 1303, which houses a primary collimator, and the collimator housing 500, which houses a secondary collimator 401. The collimator housing 500 is similar to the collimator housing 500 described above with respect to FIG. 5, and may include the primary and secondary retention mechanisms 201 and 202, contact sensor 501, all disposed on the front end 205 of the secondary collimator housing 500. At the back end 206 of the secondary collimator housing 500 is the tool changer 1300. The collimator housing 500 may include a tool plate 1302 that matches up with the tool changer 1301.

In one embodiment, the linear accelerator 101 includes an x-ray head assembly, which houses the linear accelerator, the primary and secondary collimators, RF-source, and other additional components. The primary collimator is mounted on a bulkhead of the base plate that mounts the linear accelerator, RF-source and all other components that make the x-ray head assembly. The x-ray head assembly is covered with metal enclosure to which cosmetic covers are mounted. The x-ray head assembly is mounted to the radiation treatment robot 100. The tool changer 1300 (e.g., quick change tool changer) includes a master plate 1301 and a tool plate 1302. The master plate 1301 with the lock and unlock sensors 1304, are mounted on the primary collimator 1303. The master plate 1301 of the tool changer 1300 locks to the tool plate 1302 with a pneumatically-driven locking mechanism. This locking mechanism may use a double-tapered piston with ball locking technology, as well as a fail-safe mechanism that keeps the tool plate 1302 secured to the master plate 1301 in the event of pneumatic pressure loss. Alternatively, the locking mechanism may use other components to secure the master plate 1301 and the tool plate 1302. The master plate 1301 may allow for the passage of electrical and pneumatic connections to the tool plate 1302. The tool plate 1302 may be attached to the end-effector, such as the collimator housing that engages/disengages fixed-size collimators, or the collimator housing of a variable-sized collimator. The tool plate 1302 may interface with the pneumatic and electrical connections of the master plate 1301 and passes them on to the end-effector.

Figure 14:
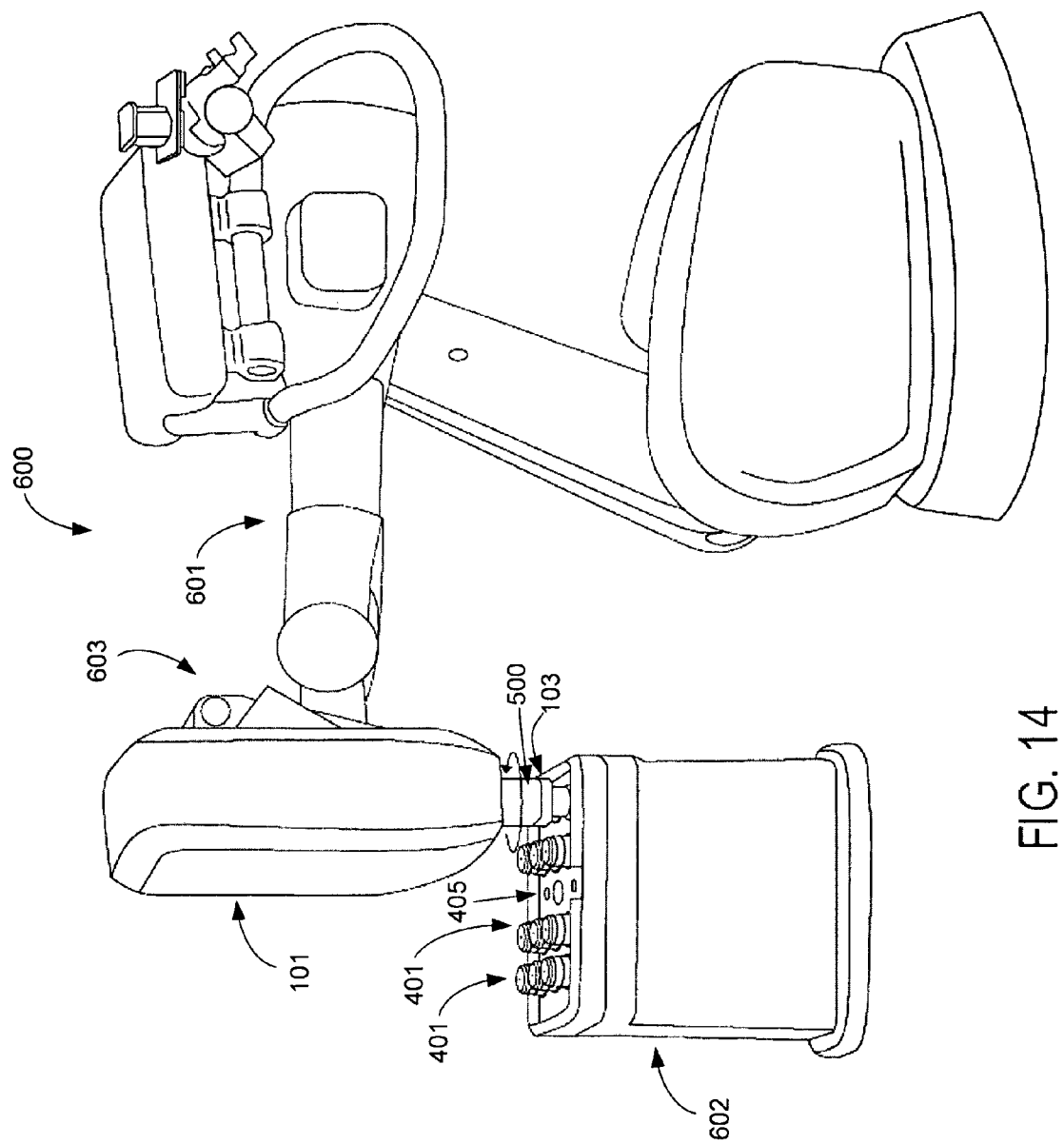
FIG. 14 illustrates one embodiment of a system including a radiation treatment robot and an automatic collimator changer for changing collimators.

FIG. 14 illustrates one embodiment of a system including a radiation treatment robot and an automatic collimator changer for changing collimators. The system 600 of FIG. 14 includes the same components as the system 600 of FIG. 6, namely, the radiation treatment robot 601 and the tool tray 602 placed within the reach of the radiation treatment robot 601. As described above, the radiation treatment robot 601 is coupled to the linear accelerator 101 via back plate 603. The system 600 also includes twelve collimators 401. These collimators may be twelve circular, fixed-size collimators. The tool tray 602 includes twelve corresponding collimator receptacle 300.

Also, as described above, the radiation treatment robot 601 and the automatic collimator changer 103 may be configured to switch one of the twelve collimators 401 from a collimator receptacle, associated with the tool tray 602, to a collimator housing 102, as well as from the collimator housing 102 to the collimator receptacle 300. FIG. 6 illustrates the radiation treatment robot 601 positioned above the tool tray 602 at a distance and FIG. 14 illustrates the radiation treatment robot 601 positioned to engage/disengage one of the collimators 401 into the collimator housing 102. As described above, the radiation treatment robot 601 may turn to lock the collimator 401 into the collimator housing 102 from the collimator receptacle 300. Alternatively, the radiation treatment robot 601 is not turned, and a pneumatic tool changer may be used for the automatic collimator changer 103 to secure the collimator 401 in the collimator housing. Although FIG. 14 illustrates picking up one collimator 401 from the tool tray 602, similarly, the radiation treatment robot 601 may be positioned to drop off one collimator 401 into an empty collimator receptacle 300 of the tool tray.

Figure 15:
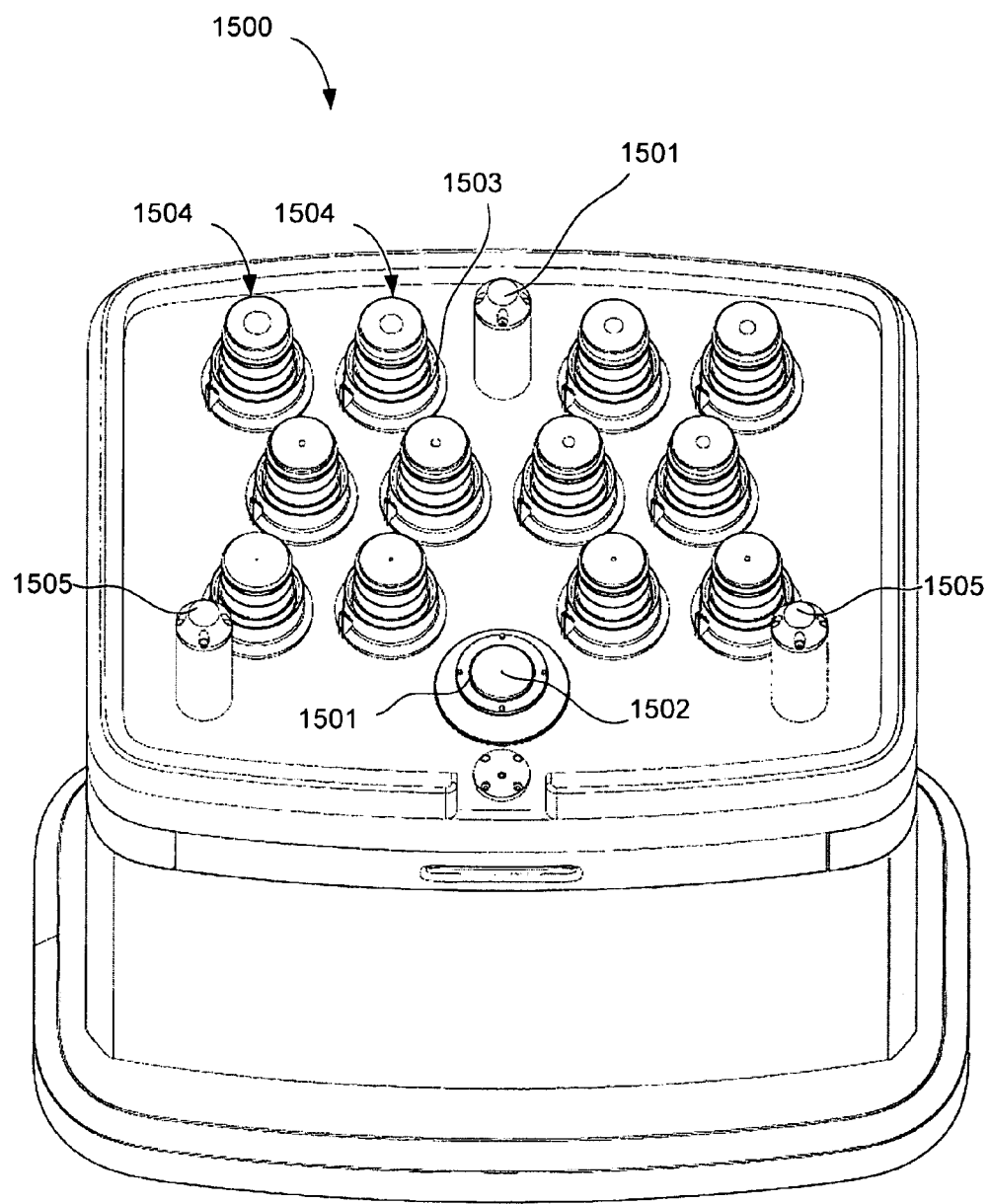
FIG. 15 illustrates one embodiment of a tool tray including a nut remover and a light sensitive sensor within the nut remover.

FIG. 15 illustrates one embodiment of a tool tray 1500 including a nut remover 1501 and a light sensitive sensor 1502 within the nut remover 1501. tool tray 1500 includes twelve collimator receptacles 1503, which house twelve collimators 1504. The twelve collimators 1504 may be circular, fixed-size collimators. Tool tray 1500 includes a nut remover 1501. The nut remover 1501 is configured to remove disengage the retention mechanisms of the automatic collimator changer 103. For example, the automatic collimator changer 103 includes primary and secondary retention mechanisms to secure the collimator 401 in the collimator housing. The primary retention mechanism is a locking nut (also referred to as a collimator retaining nut. The collimator retaining nut is removed from the collimator housing by positioning the retaining nut in the nut remover to disengage the retaining nut from the collimator housing. In one embodiment, the collimator housing is positioned over the nut remover 1501 and the alignment of the collimator housing is checked with the laser from the linear accelerator and a light sensitive sensor 1502 that is disposed within the nut remover 1501 before engaging the retaining nut of the collimator housing with the nut remover 1501. Alternatively, the light sensitive sensor 1502 is positioned in another location that within the nut remover 1501. Alternatively, no light sensitive sensors are used to check the alignment of the collimator housing and the nut remover 1502.

In one embodiment, the nut remover 1502 includes two spring pins that engage with the collimator retaining nut, which prevents the nut from rotating while the radiation treatment robot rotates (e.g., counter-clockwise) to unscrew the retaining nut from the collimator housing.

In one embodiment, a proximity switch or other type of sensor may be disposed on the nut remover 1501 to detect the presence/absence of the retaining nut in the nut remover 1501. Alternatively, no proximity switch or other type of sensor is used to detect the presence/absence of the retaining nut in the nut remover 1501.

Once the retaining nut has been removed from the collimator housing, the radiation treatment robot 100 may position the collimator housing over an empty collimator receptacle for dropping off the collimator in the collimator receptacle. The radiation treatment robot 100 may then position the collimator housing over a different collimator receptacle to pick a different collimator from the tool tray. Once the different collimator has been secured to the collimator housing (e.g., using the secondary retention mechanism), the radiation treatment robot 100 may be positioned over the nut remover 1501 to secure the collimator retaining nut (i.e., the primary retention mechanism) to the collimator housing. This may be done by positioning the collimator housing to engage the retaining nut in the nut remover 1501, and rotating (e.g., clockwise) the collimator housing using the radiation treatment robot 100 to screw the retaining nut to the collimator housing. Once the retaining nut is secured to the collimator housing, the radiation treatment robot 100 may be positioned away from the nut remover 1051 (e.g., positioned to a perch position before treatment).

Although these embodiments describe a nut as the retention mechanism and a mechanism to screw/unscrew the nut from the collimator housing, other retention mechanism removers may be employed to engage/disengage other types of retention mechanisms that may be used in the automatic collimator changer 103.

It should be noted that although discussed at times herein in regards to a robotic-based, image guided radiation treatment system, the methods and apparatus discussed herein may also be used with other types of radiation treatment systems. In alternative embodiments, other types of mechanisms such as a gantry arm or an o-ring with a gimbaled head assembly may be utilized to move a LINAC and, thereby, the collimator.

Figure 16:
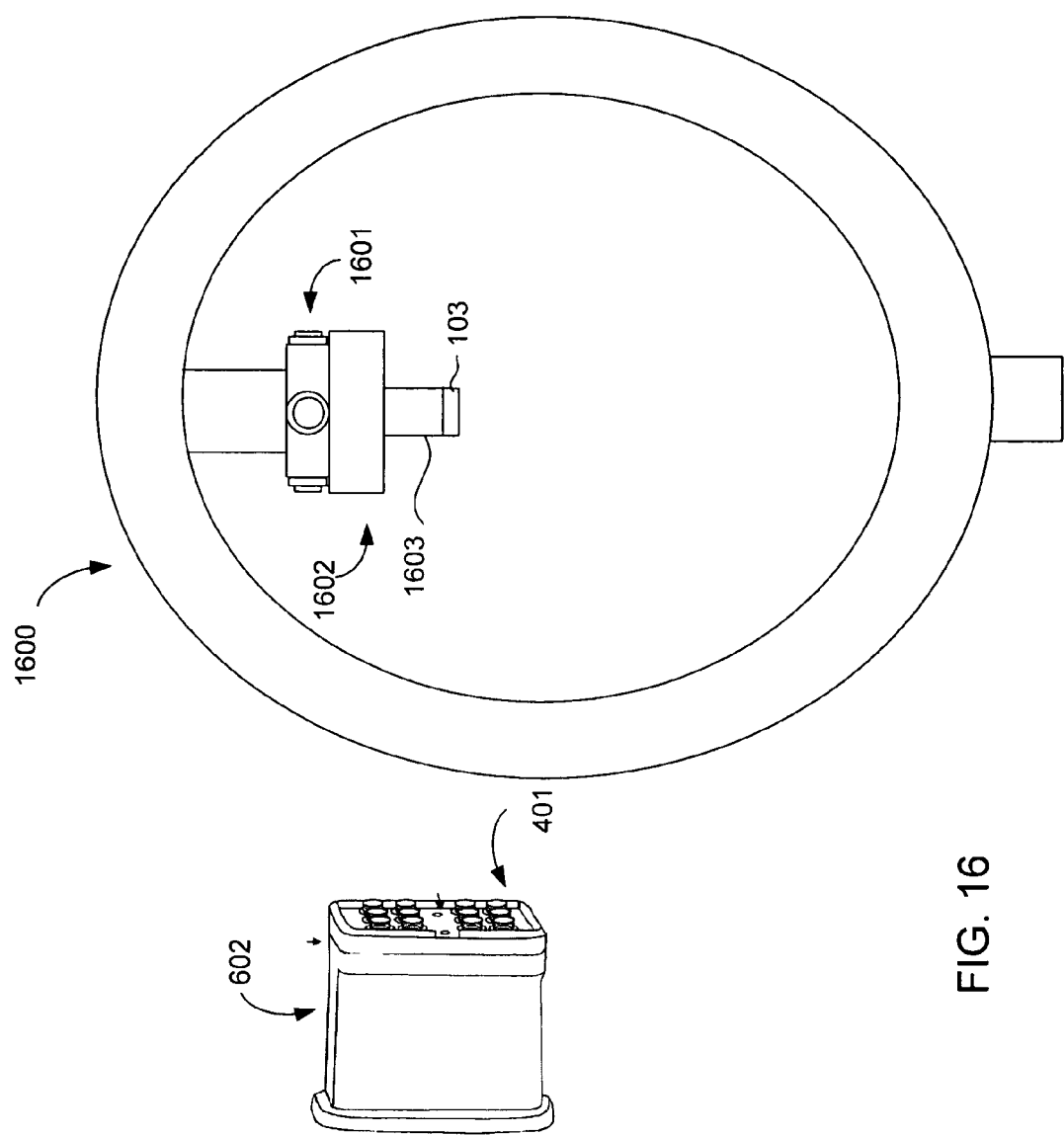
FIG. 16 illustrates one embodiment of a gantry based system having a gimbaled radiation source head assembly with an automatic collimator changer.

FIG. 16 illustrates one embodiment of an o-ring based system 1600 having a gimbaled radiation source head assembly 1601 and automatic collimator changer 103. In this embodiment, the tool tray 602 is moved under the gantry 1600 and positioned such that the linear accelerator 1602 (including a collimator housing 1603 and automatic collimator changer 103) can engage and disengage a collimator 401 in a collimator receptacle 300 of the tool tray 602. The o-ring and gimbaled head assembly 1601 may be configured to provide enough freedom of movement for the system to operate with an automatic collimator changer as described above. More specifically, the o-ring can be skewed around its vertical axis and the gimbals that can be driven to rotate in pan and tilt directions in order to position the linear accelerator 1602 to engage and disengage its collimator with the tool tray 602. The automatic collimator changer 103 includes one or more retention mechanisms, as described in the embodiments above. The collimator housing 1603, including the one or more retention mechanisms of the automatic collimator changer 103, and the movement of the linear accelerator 1602 (e.g., manipulated by the o-ring and gimbaled head assembly 1601) may be used to automatically change a collimator 401 in the collimator housing 1603. In yet another embodiment, the automatic tool changer may be used with o-ring based radiation treatment system 1600. Alternatively, the automatic collimator changer 103 may be used with other gantry based radiation treatment systems having mechanisms (e.g., arms, gimbals, etc.) to operate with an automatic collimator changer 103.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A radiation treatment system, comprising:
    a robotic arm;
    a linear accelerator mounted to the robotic arm; and
    an automatic collimator changer to automatically change one or more collimators of the radiation treatment system in coordination with the robotic arm, the automatic collimator changer comprising a collimator housing coupled to the linear accelerator and a primary retention mechanism to secure a collimator of the one or more collimators in the collimator housing, wherein the robotic arm is to move the linear accelerator to engage the primary retention mechanism.

2. The radiation treatment system of claim 1, wherein the primary retention mechanism comprises a nut.

3. The radiation treatment system of claim 1, wherein the primary retention mechanism comprises a collimator collar.

4. The radiation treatment system of claim 1, wherein the primary retention mechanism is removably coupled to the collimator housing.

5. The radiation treatment system of claim 1, wherein the primary retention mechanism is configured to positively lock on to the collimator housing.

6. The radiation treatment system of claim 4, further comprising at least one proximity switch coupled to the collimator housing to indicate when the collimator collar is secured in collimator housing.

7. The radiation treatment system of claim 1, wherein the primary retention mechanism is configured to screw on to the collimator housing.

8. The radiation treatment system of claim 1, wherein the automatic collimator changer comprises a secondary retention mechanism configured to secure the collimator in the collimator housing.

9. The radiation treatment system of claim 8, wherein the secondary retention mechanism comprises a lock pin.

10. The radiation treatment system of claim 1, further comprising a contact sensor disposed at a front end of the collimator housing, wherein the contact sensor comprises a cavity disposed on the periphery of the contact sensor, and wherein the primary retention mechanism is disposed in the cavity of the contact sensor.

11. The radiation treatment system of claim 10, wherein the primary retention mechanism comprises at least one of a lock pin, a nut, or a collimator collar.

12. The radiation treatment system of claim 10, wherein the primary retention mechanism is configured to screw on to the collimator housing.

13. The radiation treatment system of claim 1, wherein the primary retention mechanism is disposed at a back end of the collimator housing.

14. The radiation treatment system of claim 1, wherein the primary retention mechanism is disposed at a front end of the collimator housing.

15. The radiation treatment system of claim 14, wherein the automatic collimator changer comprises a secondary retention mechanism configured to secure the collimator in the collimator housing, and wherein the secondary retention mechanism is disposed at a back end of the collimator housing.

16. The radiation treatment system of claim 1, wherein the linear accelerator is coupled to the robotic arm at a back end of the linear accelerator and the linear accelerator is coupled to the automatic collimator changer at a front end of the linear accelerator, such that the linear accelerator is disposed between the robotic arm and the collimator changer.

17. A radiation treatment system, comprising:
    a robotic arm;
    a linear accelerator mounted to the robotic arm; and
    a pneumatic automatic collimator changer to automatically change one or more collimators of the radiation treatment system in coordination with the robotic arm, the pneumatic automatic collimator changer comprising a collimator housing coupled to the linear accelerator, wherein the robotic arm is to position the linear accelerator relative to a collimator of the one or more collimators, and wherein the pneumatic automatic collimator changer is to secure the collimator of the one or more collimators in the collimator housing.

18. The radiation treatment system of claim 17, wherein the pneumatic automatic collimator changer is actuated by supplying pneumatic pressure to release a secured collimator.

* * * * *